US012758394B2

(12) United States Patent
Nie et al.

(10) Patent No.: US 12,758,394 B2
(45) Date of Patent: Oct. 13, 2026

(54) DOUBLE-LAYER FIBROUS ANNULUS PATCH, PATCH CLAMP, SUTURE NEEDLE AND FISHBONE SUTURE

(71) Applicant: Shanghai Jiaotong University, Shanghai (CN)

(72) Inventors: Maodan Nie, Shanghai (CN); Chengkung Cheng, Shanghai (CN)

(73) Assignee: SHANGHAI JIAOTONG UNIVERSITY, Shanghai (CN)

(*) Notice: Subject to any disclaimer, the term of this patent is extended or adjusted under 35 U.S.C. 154(b) by 1048 days.

(21) Appl. No.: 17/951,108

(22) Filed: Sep. 23, 2022

(65) Prior Publication Data

US 2023/0210672 A1 Jul. 6, 2023

(30) Foreign Application Priority Data

Dec. 31, 2021 (CN) ........................ 202111674923.1

(51) Int. Cl.
*A61F 2/00* (2006.01)
*A61F 2/44* (2006.01)

(52) U.S. Cl.
CPC ............ *A61F 2/442* (2013.01); *A61F 2/0063* (2013.01); *A61F 2002/0072* (2013.01); *A61F 2002/0081* (2013.01); *A61F 2002/4435* (2013.01); *A61F 2210/0014* (2013.01); *A61F 2220/0075* (2013.01)

(58) Field of Classification Search
CPC ....................... A61F 2/0063; A61F 2002/4435
See application file for complete search history.

(56) References Cited

U.S. PATENT DOCUMENTS

| | | | | |
|---|---|---|---|---|
| 5,813,975 | A | 9/1998 | Valenti | |
| 10,842,603 | B1 * | 11/2020 | Street | A61F 2/0063 |
| 2003/0045937 | A1 * | 3/2003 | Ginn | A61F 2/4611 623/17.11 |
| 2007/0150064 | A1 * | 6/2007 | Ruberte | A61F 2/442 623/17.16 |
| 2007/0288040 | A1 * | 12/2007 | Ferree | A61F 2/442 606/151 |

(Continued)

FOREIGN PATENT DOCUMENTS

| | | |
|---|---|---|
| CN | 211300111 U | 8/2020 |
| WO | WO2011128334 A1 | 10/2011 |

*Primary Examiner* — Nicholas W Woodall
(74) *Attorney, Agent, or Firm* — MUNCY, GEISSLER, OLDS & LOWE, P.C.

(57) ABSTRACT

This invention relates to a double-layer fibrous annulus patch, a patch clamp, a suture needle and a fishbone suture. The inner layer foldable patch and the outer layer foldable patch are arranged and connected by a pair of crossed flexible connectors. Both ends of the two patches are connected by auxiliary connectors. A pair of auxiliary connectors are further arranged on both sides of the outer foldable patch, which can be used with the patch clamp to unfold the patch and secure it in place. With both patches in a folded state, the patch clamp is used to push the inner foldable patch through the rupture in the intervertebral disc into the annulus fibrosus and the patch unfolds within the annulus fibrosus. The outer layer foldable patch is unfolded on the outside of the annulus fibrosus and is fixed by two auxiliary connectors and fishbone sutures.

5 Claims, 4 Drawing Sheets

(56) References Cited

U.S. PATENT DOCUMENTS

| | | | | |
|---|---|---|---|---|
| 2008/0009878 | A1* | 1/2008 | McLeod | A61F 2/442 606/86 R |
| 2008/0065218 | A1* | 3/2008 | O'Neil | A61F 2/442 623/17.16 |
| 2009/0276057 | A1* | 11/2009 | Trabucco | A61F 2/0063 623/23.72 |
| 2010/0016889 | A1* | 1/2010 | Ferree | A61F 2/0063 606/228 |
| 2010/0087926 | A1* | 4/2010 | Butler | A61F 2/442 606/300 |
| 2010/0094425 | A1* | 4/2010 | Bentley | A61F 2/442 606/86 A |
| 2011/0130774 | A1* | 6/2011 | Criscuolo | A61F 2/0063 606/151 |
| 2019/0151065 | A1* | 5/2019 | Rosenblatt | A61B 17/0482 |
| 2019/0183623 | A1* | 6/2019 | Mlodinow | A61F 2/0063 |

* cited by examiner

DOUBLE-LAYER FIBROUS ANNULUS PATCH, PATCH CLAMP, SUTURE NEEDLE AND FISHBONE SUTURE

FIELD OF THE INVENTION

The invention belongs to the technical field of annulus fibrosus repair, and in particular relates to a double-layer fibrous annulus patch, a patch clamp, a suture needle and a fishbone suture.

BACKGROUND OF THE INVENTION

Human intervertebral discs are composed of three parts: cartilage endplate, annulus fibrosus and nucleus pulposus. The annulus fibrosus is a multi-layered structure, and the fibers are arranged in concentric circles with the inclination angle increasing towards the center. The nucleus pulposus is located at the center of the intervertebral disc and contains 75-90% water by net weight.

Lumbar intervertebral disc herniation is a common disease often caused by rupture of the annulus fibrosus because of degenerative changes in the intervertebral disc. The nucleus pulposus tissue protrudes from the rupture, causing irritation or compression of adjacent spinal nerve roots, resulting in symptoms such as lower back pain, numbness and pain in the lower extremities. Lumbar disc herniation has the highest incidence at L4-L5 and L5-S1, accounting for about 95%.

The most common surgery to treat a disc rupture is open surgery, in which the herniated tissue that is compressing the nerve and the proliferating bony structures is removed through a process called surgical decompression. Surgery is often traumatic and can have a prolonged recovery time.

Alternatively, Nucleotomy is a surgical procedure for removal of tissue surrounding a herniated disk, which can effectively treat lumbar disc herniation, especially in patients with recurring symptoms. The treatment does not require additional implant fixation such as screws and rods and can resolve nerve root canal stenosis caused by hypertrophy of the ligamentum flavum and facet joint hyperplasia by removing the prominent nucleus pulposus tissue. The cost of surgery is relatively low, the hospital stay is short, there is little trauma, and the recovery is quick. However, Nucleotomy, whereby the herniated nucleus pulposus is excised, does a large damage to the annulus fibrosus, but generally does not repair the rupture of the annulus fibrosus, resulting in a higher recurrence rate after surgery. In addition, the scarification of the annulus fibrosus during healing can present challenges to a second treatment in cases of re-rupture. Therefore, during discectomy, the annulus fibrosus should be repaired to reduce the postoperative recurrence rate and the incidence of other complications.

The main techniques for repairing the annulus fibrosus are direct suturing of the annulus fibrosus, tissue engineering scaffold technology, and cell and gene therapy combined with scaffolds. The following details some examples of existing technologies.

1. Annulus Fibrosus Repair Device (CN 105796165 B)

Composition:

An anchor designed to be inserted into the lower side of the end plate of the lower vertebra to fix the annulus fibrosus repair device. The device uses a blocking piece with one end connected to the anchor, while the other end is inserted into the ruptured annulus fibrosus. In order to prevent the re-herniation, the blocker should surround the posterior and upper part of the nucleus pulposus to close the rupture in the annulus fibrosus.

Operation Method:

After removing the protruding tissue, a groove is made on the surface of the first vertebral body endplate bone and a delivery device is installed at the connection between the anchor and the occluder. The anchor is then placed and the delivery handle is hammered so that the anchor is inserted into the underside of the endplate. Finally, the delivery device is removed from the repair device, and the blocker is inserted into the annulus fibrosus through the rupture to complete the blocking.

Weaknesses of the Device:

1) The vertebra has to be grooved, which causes additional damage;
2) The surface of the anchor is sharp and can easily damage the surrounding tissue. Also, the material properties of the vertebra and metal titanium are quite different, which can cause stress shielding of the bone;
3) The blocker is composed of a woven medical polyester, part of which is outside the rupture and part of which is inside the rupture. When the intervertebral disc behaves, it may drive the blocker to rub against the annulus fibrosus rupture, so it may be difficult for the rupture to heal;
4) One side of the blocker is linked to the anchor and fixed on the vertebra, but the other side is not fixed, and there is still a risk of re-herniation.

2. Annulus Fibrosus Suture Devices (1) An annulus fibrosus suture device for lumbar disc herniation after removing the nucleus pulposus using minimally invasive surgery (CN 106063714 B)

Composition:

The device includes a suture needle and a suture, with the suture needle including a guide needle wire and a guide needle sleeve. The guide needle sleeve is limited on the guide needle wire by the limiting device on the guide needle wire. The suture is connected to the guide needle wire through the suture connecting device. The guide needle wire includes a needle bar and a needle hook, and the connection between the needle bar and the needle hook is provided with a sleeve limiting body. The sleeve limiting body is an arc-shaped structure. The lower end of the guide needle sleeve is a pointed tip, and the relative position of the guide needle sleeve and the guide needle wire is limited by the sleeve limiting body and the pointed tip of the lower end of the guide needle sleeve. The needle bar, needle hook and sleeve limiting body are integrally formed structures.

The suture is fixed at the tapered tip of the suture connection device, and when the suture connection device is pulled out using a surgical needle holder, the suture connection device can be pulled out with a wire.

Operation Method:

The suture is connected to the needle hook, and the guide needle sleeve is sleeved on the guide needle wire. Pushing down the needle barrel causes the needle hook with the suture to pierce the annulus fibrosus along one side of the rupture. Maintaining the fixed needle position by hand, the guide needle sleeve is removed and the needle holder is used to remove the suture attachment from the needle hook. The guide needle wire is then removed. The other suture is then connected to the needle hook, and the guide needle sleeve is sleeved on the guide needle wire. Pushing down the needle barrel causes the needle hook with the suture to pierce the annulus fibrosus along the other side of the rupture. The ends of the stitches are knotted and trimmed to remove excess suture.

Weaknesses of the Device:

1) Suturing intervertebral discs is a complicated process with a long operation time;
2) The operation is complicated and difficult;
3) During the operation, when the wire has been passed through one side of the rupture, the other wire is brought to the other side of the rupture by holding the fixation needle. Such a fixation method is unstable and may cause secondary damage to the annulus fibrosus;
4) The suture is a single-needle suture, the closure of the rupture is poor, and the risk of re-protrusion is high.

(2) Device for single-needle positioning and suturing of the annulus fibrosus for disc herniation (CN 112401957 B)

Composition:

The device includes a channel tube, with a pneumatic component arranged in the channel tube and a suture component positioned inside the pneumatic component. The suture assembly includes a circular arc-shaped barrel, and the diameter of the arc-shaped barrel is not greater than the inner diameter of the channel tube. An arc-shaped suture needle is arranged inside the distal end of the arc-shaped cylinder, and the arc of the needle is consistent with that of the arc-shaped cylinder. The suture needle is installed in the arc-shaped cylinder, with the needle head of the suture needle facing outward, and the tail end of the suture needle connected to the arc-shaped piston.

Operation Method:

Putting pressure on the push rod drives the piston to push air into the C-shaped channel, which subsequently pushes the needle. The needle and wire are glued together and the front end of the thread is pre-knotted. As the needle is inserted it takes the wire in from one side of the rupture into the annulus and emerges from the other side of the rupture into the other end of the C-shaped channel. The C-shaped channel is provided with a strip-shaped notch and a number of bayonets. After the needle and wire reach this position, the knot will be hung on the bayonet, and the needle is reset by pulling the push rod to drive the piston to pump air. Because the knot is stuck at the bayonet, the needle and wire are separated, and another knot is tied to complete one stitch.

Weaknesses of the Device:

1) The device uses a pneumatic drive for the suture needle, which has high requirements on the tightness of the device, so it is difficult to manufacture;
2) Although the wires and needles are glued together, there is a risk of separation. The resistance encountered as the needle passes through the annulus fibrosus may cause the needle and thread to disengage under resistance from the annulus fibrosus.

(3) A hydrophilic lubricating expansion balloon for minimally invasive surgery on intervertebral discs (CN 112190822 A)

Composition:

The device includes a connecting head, with one side of the outer wall of the connecting head being provided with a channel conduit and a further inner conduit. One end of the inner conduit is connected with the balloon. The balloon is composed of a hydrophilic lubricating coating, a thermoplastic polyurethane layer, a soft polyvinyl chloride layer and a nylon layer. The outer wall of the balloon is provided with a rotary cutting needle, and the inner wall is provided with longitudinal ribs at intervals.

Operation Method:

The uninflated balloon is placed in the annulus fibrosus and the balloon is inflated through the passage conduit. In the dry state, the balloon has good toughness and the coating is evenly distributed on the surface of the balloon. The coating is colorless and transparent. In the wet state, the coating is activated by water to form a colorless and transparent hydrogel. The hydrogel coating is highly lubricated and can withstand repeated friction. The hydrogel coating also improves biocompatibility between the balloon and intervertebral disc. This can improve the mechanical strength and stability of the balloon and avoid tissue damage. The balloon is resistant to corrosion, fatigue and material aging.

Weaknesses of the Device:

1) The balloon has a large volume, which may affect the force pattern of the intervertebral disc;
2) Due to the limited surgical field of view, the balloon inflation volume is reliant on surgeon experience;
3) The nucleus pulposus is a soft aqueous substance, and the balloon may displace into it. This may compromise the stability of the rupture fixation, which can lead to re-herniation.

Therefore, Existing Products have the Following Shortcomings:

1) Because the procedures are recommended to be performed using minimally invasive surgery, all operations are performed without direct visualization of the operative site. This makes suturing more difficult and prolongs the operation time;
2) The devices are expensive;
3) In general, the rupture is not adequately sealed. The aqueous nucleus pulposus is at risk of re-herniation;
4) Most repair methods disrupt the biomechanical environment around the intervertebral disc, with a risk of secondary damage;
5) Existing products often damage the vertebra and annulus fibrosus in order to achieve fixation.

SUMMARY OF THE INVENTION

The present invention offers a simpler method for repairing a ruptured annulus fibrosus using a double-layer fibrous annulus patch, a patch clamp, a suture needle and a fishbone suture.

The double-layer annulus fibrosus patch of the present invention includes:

an inner foldable patch;

an outer foldable patch;

at least a pair of flexible connectors arranged in a cross;

in the folded state, the openings on the inner foldable patch and outer foldable patch are opposing each other; The two ends of the flexible connectors that exist in pairs are connected to diagonal corners of the inner layer patch and the outer layer patch.

Each end of the outer foldable patch contains at least an auxiliary connector, which is a wire buckle.

In the unfolded state, the inner foldable patch and the outer foldable patch are flattened, and the two flexible connectors intersect and limit the patch to the inner foldable patch and the outer foldable patch on the annulus fibrosus; The folded patches are located on the medial and lateral sides of the annulus fibrosus, respectively.

This invention is a double-layer annulus fibrosus patch, the inner foldable patch contains a first hydrophilic layer and a first support layer that are stacked; In the folded state, the first hydrophilic layer is on the inside, and the first support layer is on the outside in the folded state;

The outer layer foldable patch includes a second hydrophilic layer and a second support layer that are stacked; The second hydrophilic layer is on the inside of the folded patch and the first support layer is on the outside of the folded patch.

This invention is a double-layer annulus fibrosus patch, the fiber direction of the first hydrophilic layer is the same as the fiber direction of the inner layer of the annulus fibrosus;

The direction of fibers of the second hydrophilic layer is the same as the direction of fibers of the outer layer of the annulus fibrosus.

This invention is a double-layer annulus fibrosus patch, the first hydrophilic layer and the second hydrophilic layer have porous structures.

This invention is a double-layer annulus fibrosus patch, it also includes a memory wire, which is passed through the inner layer of the foldable patch and used to unfold the inner layer of the foldable patch after encountering the nucleus pulposus.

This invention is a double-layer annulus fibrosus patch, the flexible connectors are connecting lines, and the lengths of the two connecting lines are longer than or equal to the distance between the opposite ends of the inner foldable patch and the outer foldable patch in the unfolded state.

This invention includes a double-layer annulus fibrosus patch, the auxiliary connectors are wire buckles.

This invention includes a patch clamp, which applied to the double-layer annulus fibrosus patch, comprising:

a clamp body;

at least one pair of hooks corresponds to at least one pair of the auxiliary connectors, so that the auxiliary connectors are hung on the corresponding hooks.

this invention includes a patch clamp, the clamp is provided with a through hole for allowing the memory wire to pass through.

The present invention allows for repair of a ruptured annulus fibrosus using a double-layer annulus fibrosus patch and patch clamp through the following steps:

Step S1: The clamps on the patch clamp are folded on the outer foldable patch. The auxiliary connector is hung on the corresponding hook and the memory wire is passed through the inner foldable patch;

Step S2: The patch clamp is used to place the inner foldable patch into the intervertebral disc through the minimally invasive surgical channel, until the memory wire meets the nucleus pulposus. The inner foldable mesh is unfolded and the memory wire is removed;

Step S3: The patch clamp drives the outer foldable patch to exit the annulus fibrosus, and drives the unfolded inner layer foldable patch to stick tightly to the inner layer of the annulus fibrosus;

Step S4: The patch clamp is gradually loosened and the outer foldable patch is unfolded through the hook. After the patch clamp is completely released, it is separated from the outer foldable patch and the outer foldable patch is removed from the head of the patch clamp. The head of the patch clamp is used to flatten the outer foldable patch and rest against the outer layer of the annulus fibrosus;

Step S5: The suture needle is used to pass the fishbone suture through the annulus fibrosus on one side of the outer foldable patch and the auxiliary connector on the same side. The suture needle is advanced through the annulus fibrosus and through the auxiliary connector on the other side of the outer foldable patch to complete a needle fixation;

In step S5, the suture needle is semicircular with a radius of the curvature of 4-6 mm. Before suturing, the tip of the suture needle is placed on the annulus fibrosus, and the tail end of the suture needle is placed at the auxiliary connector.

The end of the fishbone suture is knotted, and a number of fishbone spurs are evenly arranged 1-3 mm away from the knotted end to secure the connection of the first suture and the annulus fibrosus. Then a number of fishbone spurs are arranged at intervals of 7-15 mm to secure the connection between the second suture and the fibrous annulus. The fishbone spurs are angled at 100° and the direction is consistent with the advancing direction of the suture needle.

The present invention has the following advantages and positive effects:

1. The two ends of the inner layer foldable patch and the outer layer foldable patch are respectively connected by a pair of crossed flexible connectors to form an X-shaped cross connection. Auxiliary connectors are attached to both ends of the outer foldable patch and are used with the clamp to unfold the outer layer foldable patch, as well as cooperating with the suture to fix the outer layer foldable patch on the fibrous annulus. In the folded state, the inner foldable patch is inserted through the rupture into the annulus fibrosus with a clamp, so that the inner foldable patch can be unfolded and fitted within the inner layer of the annulus fibrosus. The outer foldable patch is fixed to the outer layer of the annulus fibrosus using two auxiliary connectors and sutures. The crossed flexible connectors constrain the inner foldable patch to the inner layer of the annulus fibrosus, closing the rupture of the annulus fibrosus. The entire repair process only requires two steps of placing a clamp on the inner foldable patch and suturing the auxiliary connector and the annulus fibrosus.
2. An embodiment of the present invention is a double-layer patch design of an inner foldable patch and an outer foldable patch, which can completely block the rupture. Cells or repair materials can be implanted between the inner and outer patches to promote healing of the rupture and reduce the risk of re-herniation.
3. In an embodiment of the present invention, the inner foldable patch and the outer foldable patch are both designed with a base hydrophilic layer and an upper support layer. The hydrophilic layer assists with healing the annulus fibrosus. The support layer provides mechanical strength and can better withstand pressure on the intervertebral disc. The material of the patches can be a biological fiber material such as silk protein, which does not contain any metal components, which improves the biocompatibility of the device.
4. The hydrophilic layers are arranged on the base of the two patches and contact each side of the ruptured annulus fibrosus to assist with healing and closing the breach. The hydrophilic layer is a rough, porous structure, which is more conducive to the growth of cells, which in turn promotes the healing of the annulus fibrosus.
5. In an embodiment of the present invention, the fiber orientation of the hydrophilic layer is set to be consistent with the fiber orientation of the fibrous annulus, which can better preserve the structure and stress mode of the annulus fibrosus.
6. In an embodiment of the present invention, two thread buckles are provided on the outer foldable patch so that only two stitches are required to secure it on the annulus fibrosus. The small diameter of the suture needle mans that negligible damage is caused to the annulus fibrosus.

7. The suture needle is designed as a semi-circular needle with a radius of the curvature of 5 mm which can be rotated around the center of the circle, allowing the needle to pass through the annulus fibrosus and the thread buckle in a small space to complete the suture fixation. The whole process only touches the annulus fibrosus and the thread buckle, with little resistance to the advancing needle.
8. Fishbone spurs are located on the fishbone suture at the position where the first needle is pierced, the second needle is inserted and the position where the second needle is pierced. This arrangement can better fix the fishbone suture, the outer foldable patch and annulus fibrosus.

The fishbone spurs are angled at 100° and the direction is consistent with the advancing direction of the suture needle, which is conducive to penetration. The fishbone spurs reduce the risk of suture slippage and can reduce the risk of knots on the suture. The tips of the fishbone spurs are rounded and blunt to prevent scratching or damage to the annulus fibrosus.

Figure 1:
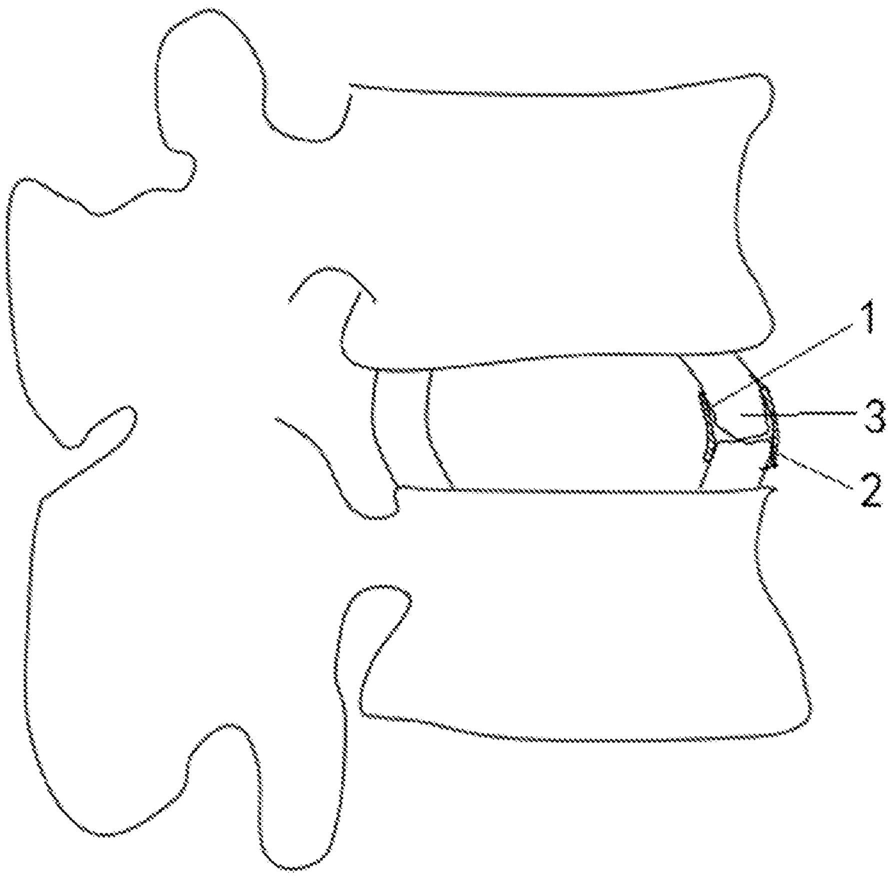
FIG. 1 is a schematic diagram of the double-layer annulus fibrosus patch of the present invention.

Description of reference numerals: 1: inner foldable patch; 2: outer foldable patch; 3: annulus fibrosus; 4: wire buckle; 5: connecting wire; 6: memory wire; 7: clamp body; 8: hook; 9: through hole; 10: suture needle; 11: fishbone suture; 12: fishbone spur.

DETAILED DESCRIPTION

The double-layer annulus fibrosus patch, patch clamp, suture needle and fishbone suture of the present invention are further described in detail below with reference to the accompanying drawings and specific embodiments.

Embodiment 1

Figure 2:
FIG. 2 is a schematic diagram of the unfolded state of the double-layer annulus fibrosus patch of the present invention.
Figure 3:
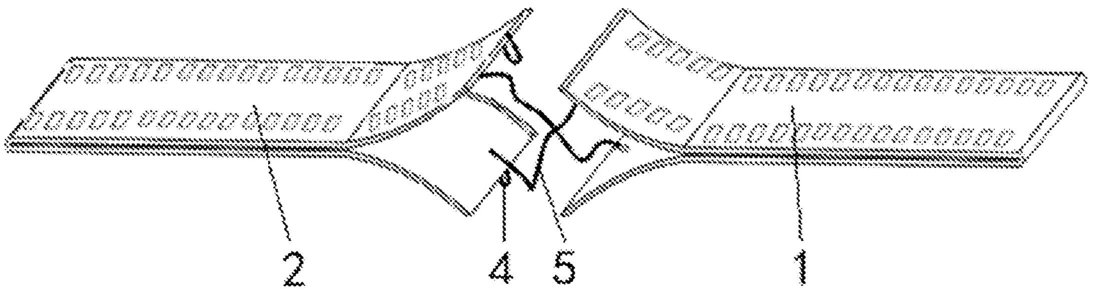
FIG. 3 is a schematic diagram of the folded state of the double-layer annulus fibrosus patch of the present invention.

Referring to FIGS. 1 to 3, the double-layered annulus fibrosus patch includes an inner foldable patch 1, an outer foldable patch 2, at least one pair of cross-arranged flexible connectors and at least one pair of auxiliary connectors.

Wherein, the openings of the inner foldable patch 1 and the outer foldable patch 2 are opposite, the two ends of the flexible connectors that exist in pairs are respectively connected to the diagonal corners of the inner foldable patch 1 and the outer foldable patch 2. The two auxiliary connectors that exist in pairs are oppositely arranged on both sides of the outer foldable patch 2. In the unfolded state, the inner foldable patch 1 and the outer foldable patch 2 are flattened, and the two flexible connectors intersect and limit the movement of the inner foldable patch 1 and outer foldable patch 2. The patches are located on the medial and lateral sides of the annulus fibrosus 3, respectively.

In this embodiment, the two ends of the inner foldable patch 1 and the outer foldable patch 2 are respectively connected by a pair of crossed flexible connectors; Further, a pair of auxiliary connectors are arranged on both sides of the outer foldable patch 2, which can be used with the clamp to unfold the outer foldable patch 2, and can also be used with sutures to fix the outer foldable patch 2 to the annulus fibrosus 3. With the inner foldable patch 1 and the outer foldable patch 2 in a folded state, the inner foldable patch 1 is passed through the rupture into the annulus fibrosus 3 using the clamp so that the inner foldable patch 1 can be unfolded and contact the inner layer of the annulus fibrosus 3. The outer layer foldable patch 2 is attached to the outer layer of the annulus fibrosus 3. The outer layer foldable patch 2 is fixed to the outer layer of the annulus fibrosus 3 with two auxiliary connectors and sutures. The inner layer foldable patch 1 is restrained in the inner layer of the annulus fibrosus 3 by the two crossed flexible connectors, thereby repairing the annulus fibrosus 3. The repair process only requires two steps, which are inserting the inner foldable patch 1 and suturing the auxiliary connector and the annulus fibrosus 3. This is a simple process and does not require repetitive threading and knotting, minimizing operative time and reducing the risk of re-herniation of the annulus fibrosus.

The double-layer patch design with an inner foldable patch 1 and outer foldable patch 2 can block an existing rupture in the annulus fibrosus. Cells, hydrogels or other repair materials can be inserted between the inner and outer patches, which can promote healing of the annulus fibrosus and reduce the risk of re-herniation.

The specific structure of the double-layer annulus fibrosus patch of the present embodiment is further described below:

In this embodiment, the inner layer foldable patch 1 includes a first hydrophilic layer and a first support layer, and the first hydrophilic layer is located inside the first support layer in a folded state. The outer layer foldable patch 2 includes a second hydrophilic layer and a second support layer, and the second hydrophilic layer is located inside the second support layer in the folded state. The hydrophilic layer and support layer of the inner foldable patch 1 and outer foldable patch 2 are stacked, and the hydrophilic layer is attached to the annulus fibrosus 3, which is conducive to the growth of cells and the healing of the annulus fibrosus 3. The support layer can provide the mechanical strength required and can better withstand the pressure of the intervertebral disc. At the same time, there is no metal in the material of the two patches, which is more biocompatible and safer.

Further, the fiber direction of the first hydrophilic layer is the same as that of the innermost layer of the annulus fibrosus 3, and the fiber direction of the second hydrophilic layer is the same as the fiber direction of the outermost layer of the annulus fibrosus 3. Setting the fiber orientation of the two hydrophilic layers to be consistent with the fiber orientation of the corresponding contact layer on the annulus fibrosus 3 can better preserve the structure and force mode of the annulus fibrosus 3.

Further, both the first hydrophilic layer and the second hydrophilic layer are porous structures. After implantation, the hydrophilic layer of the double-layer patch is fixed on both sides of the rupture. The rough, porous structure of the hydrophilic layer is conducive to the growth of cells and the healing of the annulus fibrosus 3.

Wherein, the hydrophilic layer is a porous structure woven from fibers, with good hydrophilic performance and is easily attached to the annulus fibrosus 3. As a load-bearing structure, and the use of polymer materials can provide a certain structural support.

Figure 4:
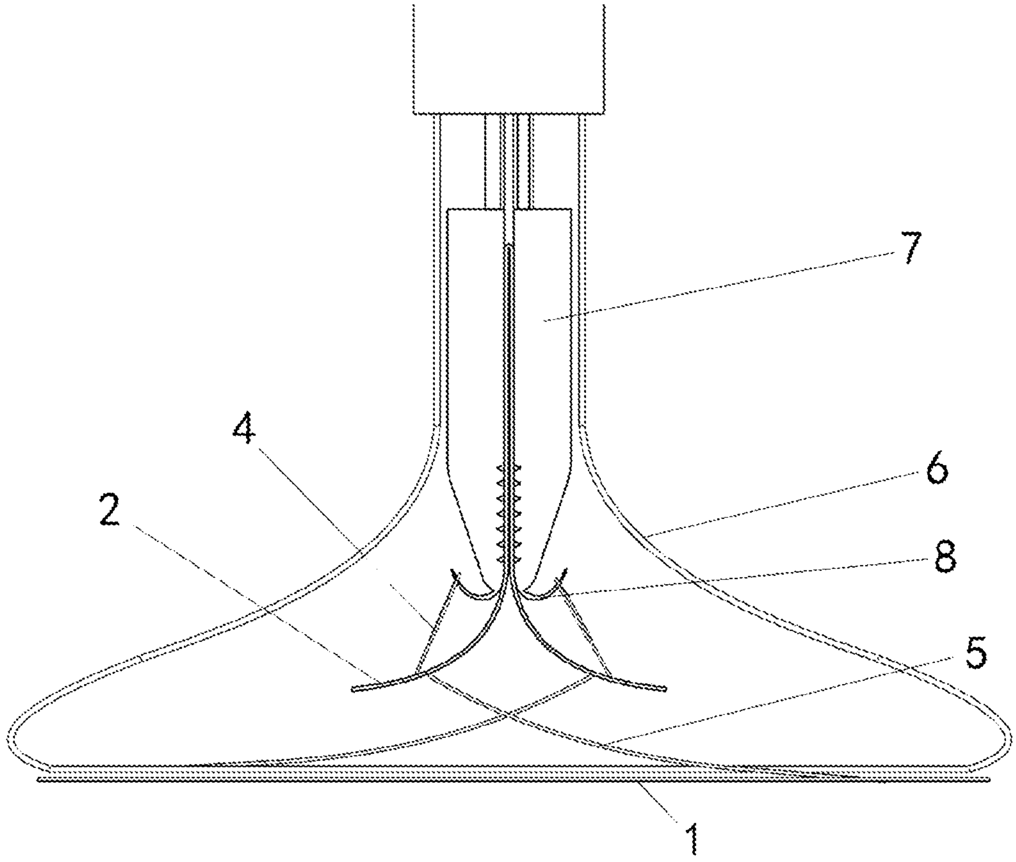
FIG. 4 is a schematic diagram of the memory wire of the double-layer fibrous annulus patch of the present invention.

As shown in FIG. 4, in this embodiment, the double-layer patch also includes a memory metal wire 6, which is passed through the inner layer of the foldable patch 1. The memory wire 6 unfolds the inner foldable patch 1 after encountering the nucleus pulposus. Specifically, the folded end of the memory wire 6 extends into the inner foldable patch 1 in the folded state. After being inserted into the ruptured annulus fibrosus 3, the folded end of the memory wire 6 returns to its original shape, thereby propping up the inner foldable patch 1.

In this embodiment, the lengths of the two flexible connecting wires 5 are both longer than the distance between the opposite ends of the inner foldable patch 1 and the outer foldable patch 2 in the unfolded state. This allows the patches to be unfolded. A small excess in the length of the connecting wire 5 will not affect the healing of the annulus fibrosus.

In this embodiment, the auxiliary connector is a wire buckle 4, and the two wire buckles 4 are respectively arranged on both ends of the outer foldable patch 2. Two wires buckles 4 are provided to facilitate the suture fixation of the patch to the fibrous annulus 3, so that the fixation of the outer foldable patch 2 only requires two stitches on the fibrous annulus 3. The small diameter of the needle minimizes damage to the annulus fibrosus 3. This procedure does not damage the vertebrae.

Embodiment 2

Figure 5:
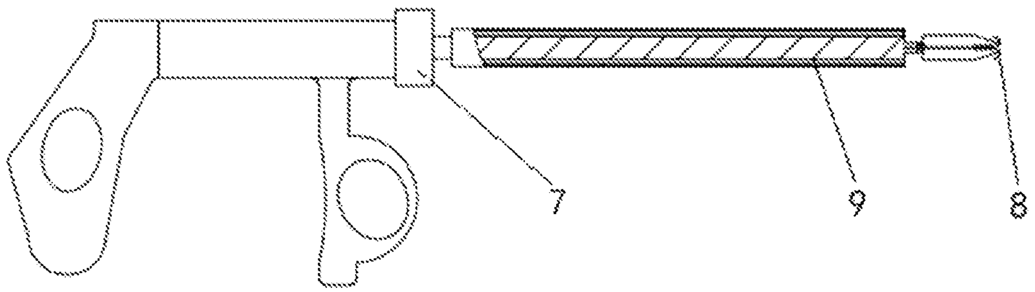
FIG. 5 is a schematic diagram of the patch clamp of the present invention.
Figure 6:
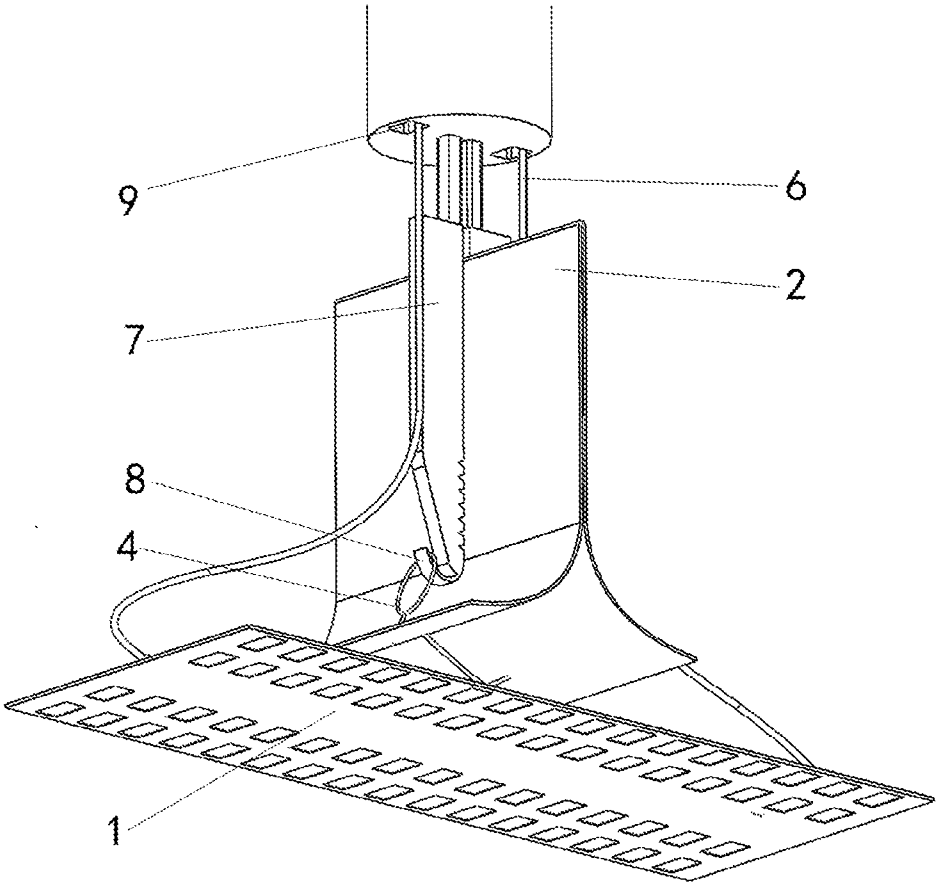
FIG. 6 is a schematic diagram of the clamped state of the patch clamp of the present invention.
Figure 7:
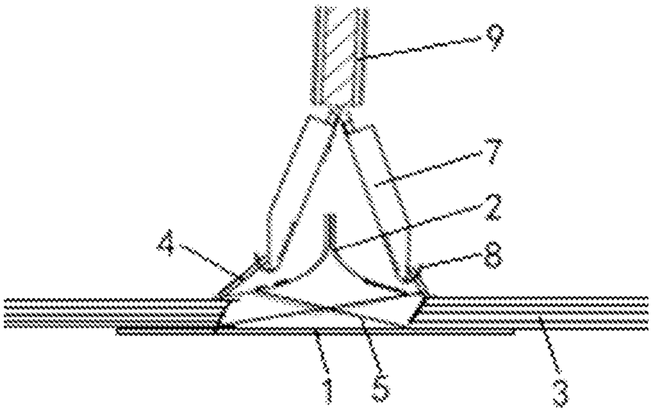
FIG. 7 is a schematic diagram of the loose state of the patch clamp of the present invention.

As shown in FIG. 5 to FIG. 7, the patch clamp to be applied to the double-layer fibrous annulus patch in Embodiment 1 includes a clamp 7 and a pair of hooks 8.

The hooks 8 correspond to the wire buckles 4 in the first embodiment, and the wire buckles 4 can be hung on the corresponding hooks 8. The clamp 7 is provided with through holes 9 for the memory wire 6 to pass through during deployment and extraction.

The following describes how the patch clamp of the present embodiment unfolds the outer foldable patch 2:

When the clamp 7 clamps the outer foldable patch 2, the hook 8 clamps the wire buckle 4. When the clamp 7 is gradually loosened, the clamp 8 gradually releases the wire buckle 4. The blunt head of the clamp 7 is used to flatten the outer foldable patch 2 against the outside of the annulus fibrosus 3.

Embodiment 3

Figure 8:
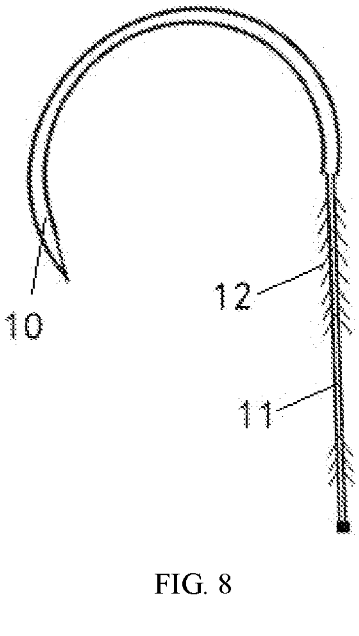
FIG. 8 is a schematic diagram of the suture needle and suture thread of the present invention.

As shown in FIG. 8, this embodiment provides a suture needle 10 and a suture 11 to be applied to the first and second embodiments above.

The suture needle 10 is semicircular with a diameter of 4-6 mm. Before use, the tip of the suture needle 10 is placed on the annulus fibrosus 3 and the tail end of the suture needle 10 is placed in the thread buckle 4 for easy positioning. During the operation, the needle is rotated around the center of the circle, so that the suture needle passes through the fibrous annulus 3 and the wire buckle 4 in a small space to complete the suture. The entire process only touches the annulus fibrosus 3 and the wire buckle 4 with little resistance to advancing the suture.

The suture is a fishbone suture 11 with eight rows of fishbone spurs 12 intermittently arranged at intervals of 7-15 mm from the base of the needle, with the remaining suture being smooth without spurs. The distance between each fishbone spur 12 is small. The end of the fishbone suture 11 is knotted and, in order to fix the first needle, three rows of fishbone spurs 12 are evenly arranged at a distance of 1-3 mm from the knot. The eight rows of fishbone spurs 12 secure the second needle. The fishbone spurs 12 are evenly arranged where the fishbone suture 11 meets the fibrous annulus 3. This method secures the fishbone suture 11 to the outer foldable patch 2 and annulus fibrosus 3.

The angle between the fishbone spurs 12 and the fishbone suture 11 is 100° and the direction is consistent with the advancing direction of the suture needle 10. This facilitates penetration of the suture and, in addition, reduces the risk of slippage of the suture 11. No knots are required during suturing. The tips of the fishbone spurs 12 are rounded and blunt to minimize scratching or damage to the annulus fibrosus 3.

Embodiment 4

This present invention allows for the rapid and effective repair of the annulus fibrosus using a double-layer annulus fibrosus patch, patch clamp, suture needle and suture thread. The operation steps are as follows:

Step S1: The patch clamp 7 holds the folded outer foldable patch 2 and the memory metal wire 6 passes through the through hole 9 and the inner foldable patch 1. The wire buckle 4 is hung on the hook 8.

Step S2: Through a minimally invasive surgical channel established by conventional surgery, the double-layer annulus fibrosus patch is placed into the intervertebral disc through the rupture using the patch clamp 7. The patch is inserted until the memory metal wire 6 encounters the nucleus pulposus and opens the inner foldable patch 1. The memory wire 6 is then removed through hole 9.

Step S3: The patch clamp 7 drives the outer foldable patch 2 to exit the annulus fibrosus 3 and drives the unfolded inner layer foldable patch 1 to press against the inner layer of the annulus fibrosus 3, with the hydrophilic layer contacting the inner surface of the annulus fibrosus 3.

Step S4: The patch clamp 7 is gradually released together with the hook 8 and the wire buckle 4 to unfold the outer foldable patch 2. After the patch clamp 7 is fully released, the hook 8 is detached from the wire buckle 4 and the outer foldable patch 2 detaches from the outer layer of the annulus 3 through the blunt head of the patch clamp 7. The hydrophilic layer on the outer foldable patch contacts the annulus fibrosus 3.

Step S5: The patch clamp 7 is then withdrawn the suture needle 10 is secured on the holder of the patch clamp 7. The suture needle 10 is pre-threaded with the fishbone suture 11. The tip side of the suture needle 10 is placed on the annulus fibrosus 3 and the tail side of the needle is placed in the thread buckle 4 on the side of the outer foldable patch 2. Rotate the suture needle 10 at the center of the semicircular needle, and thread the suture needle 10 with the fishbone suture 11 through the annulus fibrosus 3 at the front of the outer patch 2, and then through the wire buckle 4 on the same side. Using the suture needle 10 with fishbone suture 11, the other side of outer patch 2 is sutured with the same suture method. The patch is secured in place by connection between the fishbone spurs 12 and the annulus fibrosus 3. Finally, any excess suture 11 is removed to complete the fixation of the outer foldable patch 2 to the fibrous annulus 3. The fishbone suture 11 with the two wire buckles 4 confines the outer foldable patch 2 to the annulus 3.

The suture only touches the annulus fibrosus 3 and the wire buckle 4, which would provide little resistance to the advancing suture. The fishbone spurs 12 are arranged in three positions on the suture 11: at the point where the first needle passes through the inner lining of the annulus fibrosus, where the second needle passes through the inner annulus fibrosus, and after the point where the second needle passes through the outer annulus fibrosus. This allows for a more secure fixation of the patch to the annulus fibrosus 3 and a flatter suture area throughout, which reduces the risk of damage to surrounding tissues or nerves due to the fish bone spurs 12.

In other embodiments, a general suture could also be used. The suture needle 10 is pre-threaded with the suture, and the end of the suture is knotted. The tip side of the suture needle 10 is placed on the annulus fibrosus 3, and the tail side of the needle is placed in the thread buckle 4 on the side of the outer foldable patch 2. Rotate the suture needle 10 at the center of the semicircular needle, and thread the suture needle 10 with the suture through the annulus fibrosus 3 at the front of the outer patch 2, and then through the wire buckle 4 on the same side. Using the suture needle 10 with the suture, the other side of outer patch 2 is sutured with the same suture method, and finally complete the knot on the thread buckle 4. Finally, any excess suture 11 is removed to complete the fixation of the outer foldable patch 2 to the fibrous annulus 3.

The size of the rupture on the annulus fibrosus 3 can be measured using a mold test so that the most suitable patch can be selected. In this embodiment, the suture can be a single-needle suture or multi-needle suture by providing at least one pair of auxiliary connectors, which can be determined by the size of the patch. If it is equivalent in design or operation then it falls under scope, including absorbable or non-absorbable patches.

The embodiments of the present invention are described in detail with reference to text and pictures, but the present invention is not limited to the above-mentioned embodiments. Even if various changes are made to the present invention, if these changes fall within the scope of the claims of the present invention and the technical equivalents thereof, they still belong to the protected scope of the present invention.

The invention claimed is:

1. A double-layered annulus fibrosus patch, including:

an inner foldable patch;

an outer foldable patch;

a pair of flexible connectors arranged in a cross;

in a folded state, openings on the inner foldable patch and outer foldable patch are opposing each other; two ends of the flexible connectors that exist in pairs are connected to diagonal comers of the inner foldable patch and the outer foldable patch;

the outer foldable patch contains at least an auxiliary connector, which is a wire buckle;

in an unfolded state, the inner foldable patch and the outer foldable patch are flattened, and the two flexible connectors intersect and limit the patch to the inner foldable patch and the outer foldable patch.

2. The double-layer annulus fibrosus patch according to claim 1, wherein the inner foldable patch contains a first hydrophilic layer and a first support layer that are stacked, in the folded state, the first hydrophilic layer is on the inside of the folded patch and the first support layer is on the outside of the folded patch;

the outer foldable patch includes a second hydrophilic layer and a second support layer that are stacked; in the folded state, the second hydrophilic layer is on the inside of the folded patch and the second support layer is on the outside of the folded patch.

3. The double-layer annulus fibrosus patch according to claim 2, wherein the first hydrophilic layer and the second hydrophilic layer have porous structures.

4. The double-layer annulus fibrosus patch of claim 1, comprising a memory wire, which is passed through the inner foldable patch and used to unfold the inner foldable patch.

5. The double-layer annulus fibrosus patch of claim 1, wherein:

the flexible connectors are connecting lines, and lengths of the two connecting lines are longer than or equal to a distance between opposite ends of the inner foldable patch and the outer foldable patch in the unfolded state.

* * * * *